United States Patent
Istephanous et al.

(10) Patent No.: US 7,270,679 B2
(45) Date of Patent: Sep. 18, 2007

(54) IMPLANTS BASED ON ENGINEERED METAL MATRIX COMPOSITE MATERIALS HAVING ENHANCED IMAGING AND WEAR RESISTANCE

(75) Inventors: Naim Istephanous, Roseville, MN (US); Joseph Lessar, Coon Rapids, MN (US); Greg Marik, Germantown, TN (US); Darrel Untereker, Oak Grove, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 551 days.

(21) Appl. No.: 10/781,595

(22) Filed: Feb. 18, 2004

(65) Prior Publication Data

US 2004/0243241 A1  Dec. 2, 2004

Related U.S. Application Data

(60) Provisional application No. 60/474,696, filed on May 30, 2003.

(51) Int. Cl.
*A61F 2/44* (2006.01)
(52) U.S. Cl. .............. 623/17.11; 623/17.14; 623/17.15; 623/23.6
(58) Field of Classification Search .. 623/17.11–17.17, 623/23.53–23.61
See application file for complete search history.

(56) References Cited

U.S. PATENT DOCUMENTS

| | | | |
|---|---|---|---|
| 4,323,756 A | 4/1982 | Brown et al. | |
| 4,585,617 A | 4/1986 | Tenhover et al. | |
| 4,650,109 A | 3/1987 | Crivella et al. | |
| 4,687,487 A | 8/1987 | Hintermann | |
| 4,724,299 A | 2/1988 | Hammeke | |
| 4,731,115 A | 3/1988 | Abkowitz et al. | |
| 4,784,159 A | 11/1988 | Szilagyi | |
| RE32,925 E | 5/1989 | Chen et al. | |

(Continued)

FOREIGN PATENT DOCUMENTS

DE   196 41 023 A1   10/1996

(Continued)

OTHER PUBLICATIONS

Printing the Future, Medicine and Dentistry, http://home.att.net/-castleisland/faq/faq430.htm; May 15, 2007; 2 pages; Castle Island Co.

(Continued)

*Primary Examiner*—Bruce Snow
(74) *Attorney, Agent, or Firm*—Krieg DeVault LLP

(57) ABSTRACT

This invention relates to an implantable medical device to treat a patient. The implantable device can be an orthopedic device such as a spinal implant including, but not restricted to, a disc or nucleus pulposus prosthesis, a spinal rod assembly, or a bone fixation plate. The orthopedic device can be formed to include a metal matrix composite that provides enhanced wear and diagnostic imaging techniques. In other forms, the present invention provides an implantable medical device that includes a porous metal matrix composite that can deliver a therapeutic composition to a patient. In still other forms, the present invention provides an implantable electrical device or lead formed to include a metal matrix composite that provides lower polarization and interfacial impedance and allows enhanced sensing of the physiological signals.

53 Claims, 12 Drawing Sheets

U.S. PATENT DOCUMENTS

| | | |
|---|---|---|
| 4,854,496 A | 8/1989 | Bugle |
| 4,906,430 A | 3/1990 | Abkowitz et al. |
| 4,968,348 A | 11/1990 | Abkowitz et al. |
| 4,978,358 A | 12/1990 | Bobyn |
| 5,027,998 A | 7/1991 | Bugle |
| 5,043,548 A | 8/1991 | Whiteney et al. |
| 5,102,451 A | 4/1992 | Abkowitz et al. |
| 5,180,394 A | 1/1993 | Davidson |
| 5,192,323 A | 3/1993 | Shetty et al. |
| 5,246,530 A | 9/1993 | Bugle et al. |
| 5,323,954 A | 6/1994 | Shetty et al. |
| 5,326,362 A | 7/1994 | Shetty et al. |
| 5,441,537 A | 8/1995 | Kenna |
| 5,578,227 A | 11/1996 | Rabinovich |
| 5,591,233 A | 1/1997 | Kelman et al. |
| 5,758,253 A | 5/1998 | Teoh et al. |
| 5,837,960 A | 11/1998 | Lewis et al. |
| 5,925,422 A | 7/1999 | Vandenbulcke et al. |
| 5,954,724 A | 9/1999 | Davidson |
| 5,956,561 A | 9/1999 | Bugle et al. |
| 5,961,862 A | 10/1999 | Lewis et al. |
| 5,993,554 A | 11/1999 | Keicher et al. |
| 6,046,426 A | 4/2000 | Jeantette et al. |
| 6,113,637 A | 9/2000 | Gill et al. |
| 6,159,011 A | 12/2000 | Moormann et al. |
| 6,261,322 B1 | 7/2001 | Despres, III et al. |
| 6,283,997 B1 | 9/2001 | Garg et al. |
| 6,312,473 B1 | 11/2001 | Oshida |
| 6,325,868 B1 | 12/2001 | Kim et al. |
| 6,391,251 B1 | 5/2002 | Keicher et al. |
| 6,395,327 B1 | 5/2002 | Shetty |
| 6,398,815 B1 | 6/2002 | Pope et al. |
| 6,402,787 B1 | 6/2002 | Pope et al. |
| 6,410,877 B1 | 6/2002 | Dixon et al. |
| 6,419,703 B1 | 7/2002 | Fallin et al. |
| 6,520,996 B1 | 2/2003 | Manasas et al. |
| 2002/0000269 A1 | 1/2002 | Abkowitz et al. |
| 2002/0130112 A1 | 9/2002 | Manasas et al. |
| 2003/0049149 A1 | 3/2003 | Landingham |
| 2003/0060873 A1 | 3/2003 | Gertner |

FOREIGN PATENT DOCUMENTS

| | | |
|---|---|---|
| DE | 298 22 563 U1 | 12/1998 |
| EP | 0 955 021 A1 | 3/1998 |
| FR | 2 412 300 | 12/1997 |
| FR | 2 806 918 | 3/2001 |
| WO | WO 93/01771 | 2/1993 |
| WO | WO 00/23015 | 4/2000 |
| WO | WO 00/71083 | 11/2000 |
| WO | WO 02/083234 | 10/2002 |
| WO | WO 03/013396 | 2/2003 |

OTHER PUBLICATIONS

The Leader in Titanium Powder Metal Technology, http://www.dynamettechnology.com/Main_Dynalogo.htm; May 15, 2007; 1 page.

IMPLANTS BASED ON ENGINEERED METAL MATRIX COMPOSITE MATERIALS HAVING ENHANCED IMAGING AND WEAR RESISTANCE

CROSS-REFERENCE TO RELATED APPLICATION

The present application claims the benefit of U.S. Provisional Application Ser. No. 60/474,696 filed on May 30, 2003, which is hereby incorporated by reference in its entirety.

BACKGROUND OF THE INVENTION

The present invention relates to medical implants formed of a material including a metal matrix composite and to methods of implanting the implants into patients in need of treatment. The implants according to the present invention can be used to treat either chronic or acute conditions.

Currently, natural articulating bone joints and related bone structures can be replaced by ceramic, polymeric, or metallic components or a combination thereof. For example, articulating joints such as the knees, hips, and intervertebral discs can be replaced with artificial joints. It is important that the artificial joints exhibit good biocompatibility plus favorable wear characteristics, minimize any abraded or worn surfaces, and minimize the release of accompanying debris into surrounding tissues. Typically, patients undergoing hip or knee replacement are in their sixth decade of life or older. Their joint defect, disorder, and/or deterioration can occur because of a chronic condition that has become debilitating such as arthritis or osteoporosis, trauma causing a disruption in the normal joint, or degeneration as a result of the natural aging process of a patient. Current orthopedic implants typically have a useable life span of about 15 to 20 years and may perform acceptably for older patients. These implants may not need replacement during the patient's life span. However, younger patients need such devices for longer time frames. The younger patients are also more active. It is not unexpected that implants or replacement joints in younger patients are subjected to greater stress and more motion cycles than those in older patients. Conventional implants may need to be revised after some period of use in younger patients or even in active, older patients. It is desirable that the initial replacement joints survive longer periods of use (up 50 or 60 years) and withstand greater stress or strain than the present implants to avoid the likelihood of revisitation and a replacement, which is obviously a highly undesirable consequence.

It is equally important to minimize any adverse or toxicological problems associated with production of debris material from wear of the implant's articulating surfaces. Consequently, metallic implants are made of wear-resistant, physiologically-acceptable materials such as CoCr alloys.

Some metallic implants may exhibit acceptable wear characteristics; however, the same materials may also exhibit poor imaging characteristics under commonly used diagnostic imaging techniques, i.e., x-ray, fluoroscopy, CT, and MRI imaging techniques. The imaging characteristics of the implant are important and getting more so. The implant should be sufficiently radiopaque to ascertain that the implant has been properly placed and to later determine that the implant stayed in its desired location and is functioning as required. It is equally important to image/identify the soft tissue adjacent to the implant for possible adverse effects, i.e., impingement against the spinal cord or nerve roots. However, materials that are highly radiopaque tend to scatter radiation and obscure the peri-prosthetic tissue. This can make it difficult to ascertain the exact location and orientation of the implant. Additionally, the scattered radiation can obscure important details of the peri-prosthetic tissues that may be important for making regional clinical diagnoses. Additionally, the desired degree of radiopacity (or radiolucency) may vary depending upon the mode of treatment, treatment site, and type of implant.

Until now, the selection of materials having varying physical and mechanical properties for medical implants has been limited. In general, traditional materials that exhibit good wear characteristics tend to have poor imaging properties. Other materials have acceptable imaging characteristics but unfavorable wear performance.

Consequently, in light of the above problems, there is a continuing need for advancements in the relevant field. These advancements include new implant designs, medical devices, and new material compositions for use in the medical field. The present invention is such an advancement and provides a variety of additional benefits and advantages.

SUMMARY OF THE INVENTION

Figure 1:
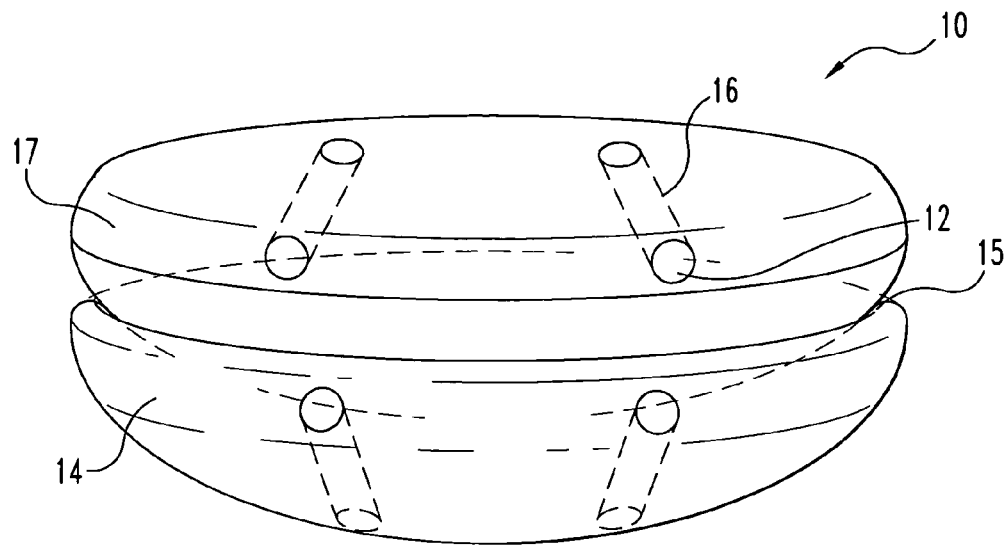
FIG. 1 is a perspective view of one embodiment of a disc prosthesis assembly in accordance with the present invention.

In one form, the present invention provides a spinal implant assembly for insertion between two adjacent vertebrae. The implant comprises a first structural member including a first surface configured to engage the first vertebrae and an opposite second surface; and a second structural member including a third surface configured to engage the second vertebrae and an opposite fourth surface having a bearing portion configured to engage the second surface of the first structural member. The first and second structural members in this embodiment of the invention comprise a composite including a metallic matrix and a reinforcing component dispersed within the metallic matrix. The reinforcing component can be homogeneously distributed throughout the metal matrix composite. In other embodiments, the reinforcing component can be dispersed either in-homogeneously or as a gradient throughout the metal matrix composite.

The metallic matrix can include, but is not limited to, one or more of the following materials: titanium, titanium aluminum alloy, zirconium, and niobium. The reinforcing component can be a ceramic or an inter-metallic material. Non-limiting specific examples of the reinforcing component include TiC, $TiB_2$, TiN, TiAl, WC, $BC_4$, BN, diamond, $ZrO_2$, $Al_2O_3$, and mixtures of these materials.

The metal matrix can include a widely varying amount of the reinforcing components. Preferably, the metal matrix composite comprises between about 10 wt % and about 90 wt % of the reinforcing component based upon the total weight of the metallic matrix composition. Alternatively, the metal matrix comprises between about 10 wt % and about 80 wt %; in still another alternative, the metallic matrix comprises between about 10 wt % and about 40 wt % of the reinforcing component. Implants according to the present invention can be fabricated to exhibit widely varying physical characteristics. For example, the metal matrix can be fabricated through processes such as sintering to have a density as desired for a particular application. In selected applications, the density can be greater than about 85%, more preferably greater than about 90%, and more preferably approaching 100%. Further, the metal matrix composite according to the present invention can exhibit varying degrees of hardness, again depending upon the desired application. In other embodiments, the metal matrix composite can be provided as a porous material. The porous material can serve as a depot for a therapeutic agent and control the release of that therapeutic agent into surrounding tissue. In other embodiments, the properties can be tailored as desired to allow bone ingrowth. Consequently, the properties, percent porosity, average pore size, pore depth, and volume can vary widely depending upon the intended application of the material.

In another form, the implants of the present invention are fabricated to create a spinal implant. The spinal implant can include a first and second plate and can be used in any application which requires an articulating joint. The first and second plate can be configured to matingly match their respective geometries to allow a smooth, facile translation and/or rotation.

In another form, the present invention provides a spinal implant assembly for insertion between adjacent vertebrae. The spinal implant assembly comprises a first structural member and a second structural member. The first structural member can include a first surface configured to engage a first vertebrae and an opposite second surface having a first recess therein. The second structural member can include a third surface configured to engage the second vertebrae and an opposite fourth surface having a second recess configured to oppose the first recess in the first structural member. An articulating element is disposed between the first recess and the second recess. One or more of the articulating element, the first structural member, and the second structural member can comprise a metal matrix composite that includes a metallic matrix and a reinforcing component dispersed within the metallic matrix.

In this embodiment, the articulating element can be provided in a wide variety of configurations including, but not limited to, spherical, cylindrical, or elliptical geometries.

In yet another form, the present invention provides a medical device. The medical device comprises an implantable portion for treatment or diagnosis of a patient. The implantable portion can include a first layer comprising a metal matrix composite that includes a metal matrix and a reinforcing component dispersed within the metal matrix. The medical device can be fabricated in a wide variety of implantable medical devices including, but not limited to, a disc prosthesis, a bone plate, a catheter, a catheter tip, an electrode lead for a pacemaker, and other stimulation electrode. As noted above, the metal matrix composite and reinforcing component can be selected from a wide variety of materials. The specific materials are noted above for the other identified embodiments.

In yet another form, the present invention provides a method of treating a spinal defect and/or disorder. The treatment method includes preparing a disc space between two adjacent vertebrae to receive a spinal implant, inserting a spinal implant assembly, which assembly includes a first structural member having a first surface to engage a first vertebra and an opposite second surface, and a second structural member having a third surface to engage an adjacent vertebra and an opposite fourth surface to bear against the second surface of the first structural member. At least one of the first structural member or second structural member is/are composed of a metal matrix composite that includes a metal matrix including a biocompatible metal or metal alloy and a reinforcing component disposed within the metallic matrix. The treatment in accordance with the present invention can also include performing a discectomy to remove all or a portion of the dissected disc structure between the adjacent vertebrae. Additionally, the spinal implant assembly can incorporate a therapeutic agent to treat a medical condition and/or induce bone growth or tissue ingrowth into the implanted assembly.

In each of the embodiments of the present invention, the medical devices or implants can be fabricated to exhibit a wide variety of desirable characteristics including a selected radiolucency which may vary depending upon the mode of treatment, the volume of tissue being treated, and type of device.

The devices can be fabricated from a substrate material, such as the metal matrix composite, that exhibits the desirable physical characteristics. Further, when desired for specific applications, the substrate material can be coated with additional coatings or layers or further treated, i.e., a surface treatment such as nitriding, carburizing, or carbonitriding.

It is an object of the present invention to provide implants based on engineered metal matrix composite materials having enhanced imaging and wear resistance.

DETAILED DESCRIPTION OF THE INVENTION

For the purposes of promoting an understanding of the principles of the invention, reference will now be made to the embodiments illustrated herein, and specific language will be used to describe the same. It will nevertheless be understood that no limitation of the scope of the present invention is hereby intended. Any alterations and further modifications in the described medical devices, metallic matrix composites or methods for treating patients, and any further applications of the principles of the invention as described herein, are contemplated as would normally occur to one skilled in the art to which the invention relates.

The present invention includes implantable medical devices at least partly formed from a metal matrix composite, for example, metal matrix composites may be overlaid on a metallic substrate. Specific examples of medical devices that are included within the scope of the present invention include: orthopedic implants, such as spinal implants, disc prostheses, nucleus prostheses, bone fixation devices, bone plates, spinal rods, rod connectors, knees, hip prostheses; cranial implants; drug delivery implants such as stents, implantable tubes or capsules, and catheter tips; electrical conducting leads, such as leads for sensors, pacemakers, and electrodes, i.e., a stimulation electrode or a monitoring electrode; cardiovascular implants, such as stents; and the like. The medical devices of the present invention can be used to treat a wide variety of animals, particularly vertebrate animals and including humans.

The medical devices based on this invention are formed of novel materials for use in implantable medical devices. In one embodiment, the present invention provides an orthopedic device that exhibits enhanced wear characteristics. These devices are particularly advantageous for use in articulating joints such as spinal implants and disc or nucleus prostheses, which are used to treat spinal defects. In another embodiment, the present invention provides medical devices that include a porous metallic structure that can be fabricated as a composite. The porous structure can facilitate tissue ingrowth into the implanted medical device. In addition or in the alternative, the porous structure can be impregnated with a therapeutic agent such as a drug, growth factor, proteins, and the like, to elicit a targeted chronic or acute biological response. Pore characteristics such as size and depth can be engineered to attain a desired elution rate (acute or chronic) of one or more therapeutic agents. In other embodiments, the porous structure can provide a substrate with a surface layer that can adhere and retain a coating via a mechanical interlocking mechanism. The applied coating can be a metallic coating, a polymeric coating, or a coating employing endogenous materials. The coating and/or the underlying porous structure can be impregnated with a therapeutic composition to treat one or more medical conditions.

FIG. 1 is an elevated side view of one embodiment of disc prosthesis 10 for implantation in a disc space between a pair of vertebrae in accordance with the present invention. Prosthesis 10 is illustrated comprising two basic components: a first structural member, such as a first plate 12, and a second structural member, such as second plate 14. First plate 12 and second plate 14 bear against each other at interface 15.

Figure 2:
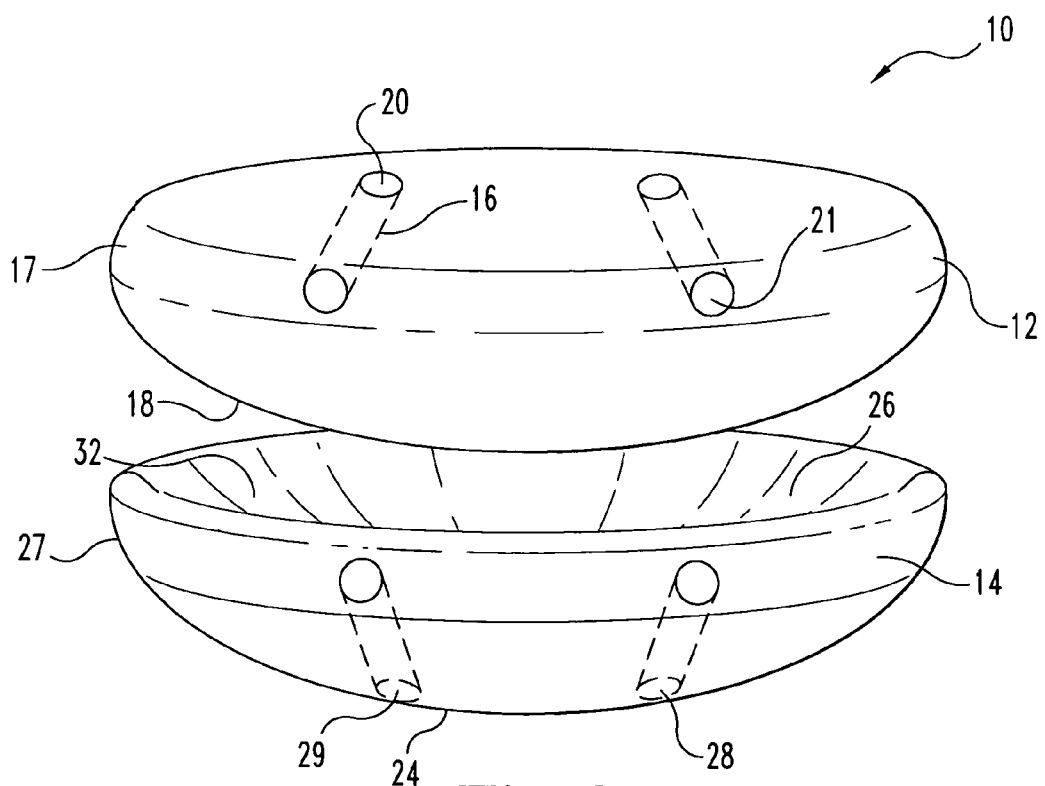
FIG. 2 is an exploded, elevated, side view of the disc prosthesis of FIG. 1.

FIG. 2 is an exploded view of prosthesis 10. First plate 12 comprises a first surface 16 as an upper bone engaging surface, an opposite second surface 18, and a sidewall 17 therebetween. First surface 16 is provided in a configuration selected to engage with a first, opposing vertebral endplate (not shown). First surface 16 can include a curved surface portion to matingly conform with and engage with the endplate of the opposing vertebra. In the illustrated embodiment, first surface 16 can be configured to engage with the inferior endplate of a cervical vertebral body. However, it will be understood that prosthesis 10 can be sized to be inserted between any two articulating vertebrae, for example, thoracic, lumbar, and even between the L5 lumbar and the S1 sacral vertebrae.

In alternative embodiments, first surface 16 can either be substantially planar or have a flat surface portion. It will also be understood that the endplate of a particular vertebra can be cut and/or shaped during surgery to receive the disc prosthesis and to securely engage with a planar first surface 16.

First surface 16 can include one or more bone engaging structures on the entire surface or surface portions, to ensure secure attachment to the vertebra. Examples of bone engaging structures include teeth, ridges, grooves, rails, a porous surface layer, coating layer(s) formed of a different metallic material, a polymeric material, or a ceramic material (e.g. hydroxyapatite, and the like). Further, plate 12 can have one or more openings, apertures, or bores 20 and 21 through which a bone fastener such as a screw (not shown) can be inserted to secure plate 12 to the vertebral body.

In other embodiments, first surface 16 can be formed of a metal matrix composite material, metal, or alloy that exhibits a predetermined, or controlled or selected porosity. The pore size can be varied as desired for a use in a particular application. For example, the pore size can be selected to allow bone ingrowth into the metal matrix composite. In this embodiment, the pore size can be controlled or selected to be between about 10 microns ($\mu$) and about 500$\mu$. Alternatively, the pore size can be between about 25$\mu$ and about 200$\mu$; or between about 50$\mu$ and 150$\mu$ as desired for a particular application.

The pore size can also be controlled or selected to facilitate use of the implant as a depot for one or more therapeutic agents or to facilitate the release of therapeutic agents into adjacent tissue. Further, the pore size can be varied and optimized, as desired, to allow a controlled delivery rate of the agents(s); the controlled delivery rate can be for either chronic and/or acute treatment.

Second plate 14 comprises a third surface 24, an opposite fourth surface 26, and a side wall 27 therebetween. Third surface 24 is provided in a configuration to engage with the endplate of an opposing vertebra (not shown) similar to first surface 16. In the illustrated embodiment, surface 24 is configured to engage with the superior surface of a cervical vertebra. Further, third surface 24 also can include bone engaging structures including teeth, ridges, grooves, keel, rails, a porous surface layer, coating layer(s) as noted above, and/or one or more apertures or bores 28 and 29. A bone fastener, such as a screw, can be inserted through each of the one or more apertures 28 to secure plate 12 to the bone tissue.

In use, when inserted between a disc space between two adjacent vertebrae, second surface 18 and fourth surface 26 exhibit a sliding and/or rotating engagement with each other. Consequently, second surface 18 and fourth surface 26 are individually shaped to matingly conform to each other. In the illustrated embodiment, second surface 18 exhibits a convex shape, and fourth surface 26 exhibits a concave shape. Each of second surface 18 and fourth surface 26 define wear surfaces 30 and 32, respectively, which are formed of a material selected to exhibit enhanced wear characteristics. The material can be selected as a metal matrix composite with a reinforcing component uniformly or non uniformly dispersed therethrough. In preferred embodiments, surfaces 30 and 32 are characterized to have a minimum surface hardness of greater than about 20 Rc; more preferably, greater than about 45 Rc. With increasing amounts of the reinforcing component, the surface hardness can increase.

In one embodiment, first plate 12 and second plate 14 comprise a metal matrix composite that includes a base metal or metal matrix with a reinforcing component interspersed therein. It should be understood that in this embodiment, the reinforcing component is not just a surface coating of the reinforcing component. The reinforcing component has been dispersed either homogeneously or in-homogeneously throughout the matrix or the matrix layer. Incorporation of reinforcing component throughout the matrix or matrix layer provides a metal matrix composite that exhibits "bulk hardness". The metal matrix composite can exhibit varying properties or characteristics selected to provide enhanced wear characteristics. The metal matrix composite is discussed more fully below. In one form, the metal matrix composite exhibits a density approaching 100%. By use of the term 100% dense, it is intended to mean that the composite is non porous. In other embodiments, the metal matrix composite exhibits a density that can be varied depending upon the desired application. In other embodiments, one or more of the first or second structure members can have a less dense core. This can be accomplished by selectively increasing the porosity of the core.

Prosthesis 10 is illustrated to exhibit a bi-convex lens, cross sectional shape. In other embodiments, it will be understood that the shape of prosthesis 10 can be varied to include a wedge shape or lordotic shape to correct or restore a desired disc space height or spinal column orientation.

Prosthesis 10 can be provided in a size and a shape to promote the desired therapy to treat the spinal defect. Consequently, prosthesis 10 can be provided in a size to fit between adjacent vertebrae such as the cervical vertebrae, the thoracic vertebrae, the lumbar vertebrae, and the sacral vertebrae. Prosthesis 10 can be sized to extend laterally across the entire surface of the endplate of the opposing vertebrae. More preferably, prosthesis 10 can be sized to extend laterally to bear against the apophyseal ring structure. Prosthesis 10 can extend anterior and posterior across the entire endplate of the opposing vertebrae. In the illustrated embodiment, when viewed from above, prosthesis 10 is configured to resemble a shape with a matching geometry to interface with the opposing endplates of the adjacent vertebrae.

In one embodiment, first plate 12 and second plate 14 each can be formed as a monolithic metal matrix composite. The metal matrix composite composing the first and second plates 12 and 14 can comprise a metal matrix including a titanium matrix or a titanium alloy. A reinforcing component is dispersed throughout the metal matrix. The matrix material and the reinforcing component are discussed more fully below.

In other embodiments, first plate 12 and second plate 14 can be made of one or more layers or regions. The one or more layers can be either vertical layers, i.e., layered or laminated one on top of another from first surface 16 to second surface 18 or horizontal layers laminated laterally and/or anterior-posterior, side by side each other (considering the placement of the implant in the spinal column). The different layers or regions can be composed of the same or different metal matrices or composites (different alloy systems). If the different layers contain different composites, the different composites can contain different constituents or the same constituents in differing amounts. For example, first surface 16 can be formed of a first material that includes a first metal matrix composite having a first reinforcing component dispersed therein or, alternatively, no reinforcing component therein. Preferably the first metal matrix composite can be provided to exhibit a selected porosity sufficient to allow tissue integration or ingrowth to enhance the secure attachment of the implant to the vertebra and/or delivery of therapeutic agents. Second surface 18 can be formed of a second material selected to enhance the wear capability and increase the useable life span of the implanted prosthesis. For example, second surface 18 can be formed of a second metal matrix material having a sufficient hardness to reduce wear or material loss from the surface in use. Additionally, the residual body portion of second plate 14 can be formed of yet another material selected to enhance the image capabilities of the implant when examined using common diagnostic imaging techniques, such as x-ray (including fluoroscopy), CT, or MRI scanning techniques. Consequently, second plate 14 can be provided as a laminated structure with two, three, or more layers. The metal matrix material and/or the reinforcing component in the composite or their concentrations can differ between the different layers.

Alternatively, second plate 14 can be provided as a single material formed of a metal matrix composite having the reinforcing component distributed therethrough in a homogeneous or non-homogeneous manner. In other embodiments, the reinforcing component can be dispersed within the matrix in a concentration gradient that varies from the second surface 18 to the first surface 16. The relative concentration of the reinforcing material in the matrix can increase from a low value proximate to first surface 16 to a maximum value near or at second surface 18.

In still yet other embodiments, the identity of the reinforcing component or the metal matrix material can vary or change from the different layers or even between different regions of the prosthesis.

Additionally, a third structural member can be positioned between the first plate 12 and second plate 14. This third structural member, attached or floating, can comprise a polymeric, ceramic, or metallic material. The metallic material can be the same or different from the metal matrix composite. The polymeric material can be either biodegradable or biostable, examples of which are discussed more fully below. In one form, this third structural component can comprise a uniform plate with a round, oval, or endplate matching configuration. In other forms, the third structural member can comprise a donut-like shape. The interior cavity of the "donut" may or may not be filled with a therapeutic agent.

Figure 3:
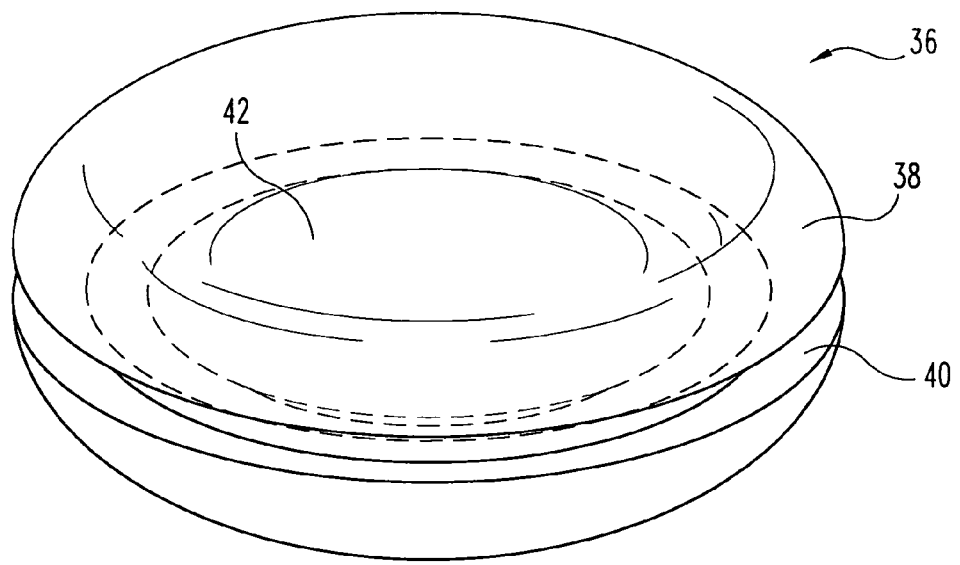
FIG. 3 is a perspective view of an alternative embodiment of a disc prosthesis assembly in accordance with the present invention.
Figure 4:
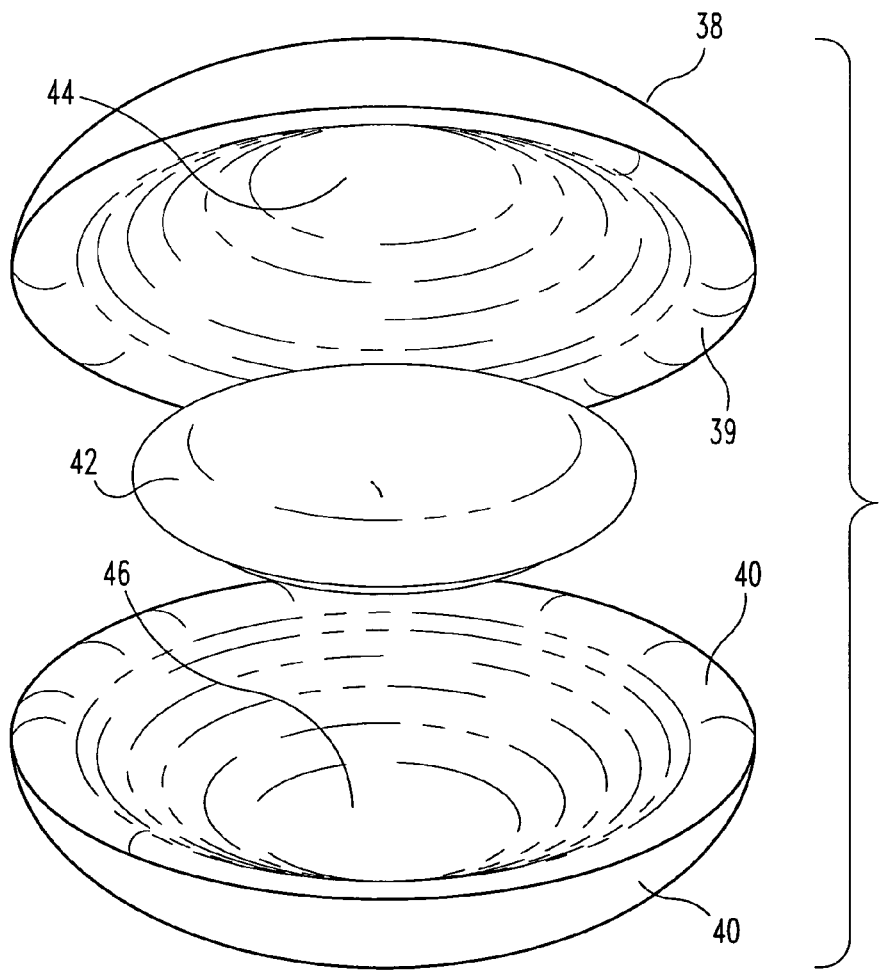
FIG. 4 is an exploded view of the disc prostheses assembly of FIG. 3.

FIG. 3 is a perspective view of an alternative implant assembly 36 in accordance with the present invention. Implant assembly 36 includes an upper, or first plate 38, an opposing, lower or second plate 40, and an articulating element 42 disposed therebetween. Referring additionally to FIG. 4, articulating element engages or rests within a first depression, receptacle, or recess 44 in first plate 38 and in an opposing depression or second receptacle 46 in second plate 48.

Articulating element 42 is illustrated as a curved element, preferably having an ovoid shape and/or having a round or oval cross-sectional shape. Alternatively, articulating element can be provided in a variety of other shapes including spherical, cylindrical or elliptical, disk shape, flattened shape, or wafer and the like.

Articulating element 42 can be composed of a metallic material, preferably a metal matrix composite as discussed herein.

First plate 38 can be provided substantially as described above to first plate 12 for implant 10, including the bores for bone fasteners, such as screws, and bone engaging surfaces. Additionally first plate includes recess 44 on its underneath surface 39, opposite the upper or bone engaging surface 41. Recess 44 can be composed or coated with a layer of material that is the same or different from the material forming the bulk of first plate 38. Preferably the layer of material coating the recess 44 is composed of a metal matrix composite. The metal matrix composite can be the same or different from the material that forms the articulating element 42.

Second plate 40 can be formed similar to first plate 38 including the bores and bone engaging surfaces. Further, second plate 40 includes a second recess 46 that can oppose first receptacle 44 when the implant is fully assembled. Recess 46 can be configured and formed similar to that described above for receptacle 44 including the selection of material and/or coating or layer of material such as the metal matrix composite that is different from that forming the bulk of the second plate 40.

Figure 5:
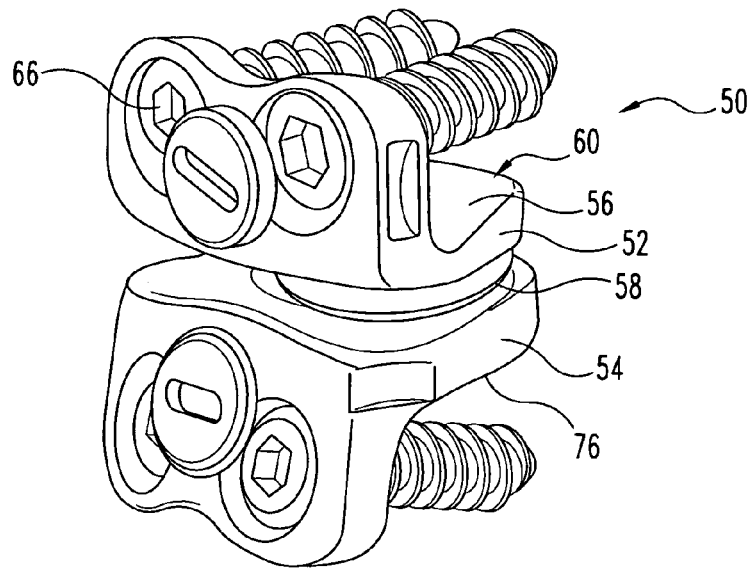
FIG. 5 is a perspective view of one embodiment of a spinal cervical implant in accordance with the present invention.
Figure 6:
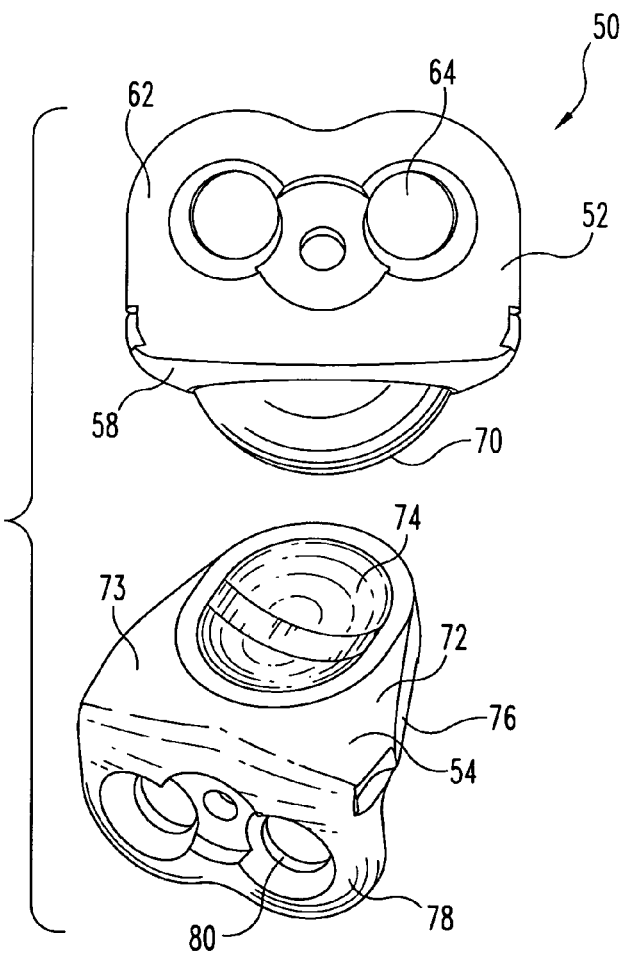
FIG. 6 is an exploded view of the spinal implant of FIG. 5.

FIG. 5 illustrates an alternative embodiment of a prosthesis or spinal implant 50. Implant 50 includes exterior configuration similar to that which has been previously described in U.S. Pat. No. 6,113,637, which is hereby incorporated by reference in its entirety. Implant 50 includes an upper portion 52 and a lower portion 54. Referring additionally to FIG. 6, which is an exploded view of implant 50, upper portion 52 is spaced from lower portion 54. Upper portion 52 includes a first surface 56 and an opposite, second surface 58.

In the illustrated embodiment, first surface 56 is substantially planar. However, as described above for implant 10, first surface 56 can be provided to include a wide variety of features or structures selected to engage with the endplate of an opposing vertebra. Examples of tissue-engaging structures include teeth, ridges, pores, grooves, roughened surfaces, wire mesh, and the like. Additionally or in the alternative, surface 56 can include tissue-engaging structures such as ridge 60 illustrated. A first flange 62 extends from upper portion 52. Flange 62 can have one, two, or more apertures 64 extending therethrough. Aperture 64 can be a smooth bore or a threaded bore. A bone fastener 66 can be threaded or inserted through aperture 64 and then secured into bone tissue. Bone fastener 66 can be any bone fastener known, described, and/or commonly used for orthopedic applications including screws, staples, wires, pins, rods, sutures, and the like.

A protuberance or hemi-spherical projection 70 extends downwardly from second surface 58. Projection 70 defines a bearing surface that engages with lower portion 54. In one embodiment, projection 70 is formed of a first metal matrix composite. The first metal matrix composite exhibits a hardness selected to enhance and extend the useful life span of the implant as it operates or is intended to operate as a disc prosthesis with minimal wear and limited debris loss to the surrounding environment and tissue. The first metal matrix composite can be the same material or a different material used to form the residual portion of second surface 58 and/or the upper portion 52.

Lower portion 54 includes a third surface 72, which has a trough 74 formed therein. Trough 74 is configured to receive or seat projection 70 therebetween. In one preferred embodiment, trough 74 is configured to allow projection 70 and consequently upper portion 52 to rotate or partly rotate about three orthogonal axes and translate or slide along in at least one direction. Preferably trough 74 allows upper portion 52 to slide in the anterior to posterior (AP) direction, referring to the orientation (translation) of the prosthesis in the disc space.

In some embodiments, the upper portion 52 and lower portion 54 can, but need not, be formed of the same material. For example, upper portion 52 can be formed of a first biocompatible material, which may or may not be a metal matrix composite and lower portion 54 can be formed of a second biocompatible material, different from the first material. The second material also, can, but need not, be formed of a metal matrix composite.

When desired, the non-metal matrix composite materials can comprise one or more of a polymeric material—either biodegradable or not, a ceramic material, a metallic material, or a pure metal or alloy material.

At least, the trough portion 74 of the third surface 72 is formed of a metal matrix composite that exhibits enhanced wear characteristics. Preferably, the third surface 72 and the body 73 of lower portion 54 are formed of the same metal matrix composite.

Lower portion 54 also includes a fourth surface 76 opposite the third surface 72. Fourth surface 76 can be provided to securely engage with the opposing vertebra and can include tissue engaging structures as has been described above for the first surface 56. Further, lower portion 54 can include a second flange 78 extending therefrom. Second flange 78 can be configured substantially as has been described for first flange 62, including one or more bore or apertures 80 through which bone fasteners can be inserted to engage with underlying tissue.

In alternative embodiments, protuberance 70 is separable or non-integral with second surface 58 of upper portion 52. Instead, second surface 58 includes a recess or trough similar to trough portion 74 formed therein. The non-integral protuberance 70 is disposed between trough 74 and the trough formed in second surface 58. The non-integral protuberance can comprise a metal matrix composite that is the same or different from that included in either the upper portion 57 or lower portion 54. Further, the non-integral protuberance can be provided in a wide variety of shapes including round, or spherical, elliptical, and cylindrical. In these embodiments, protuberance 70 can comprise any biocompatible material including polymers—either biodegradable or not, metallic materials, and metal alloys.

Figure 7:
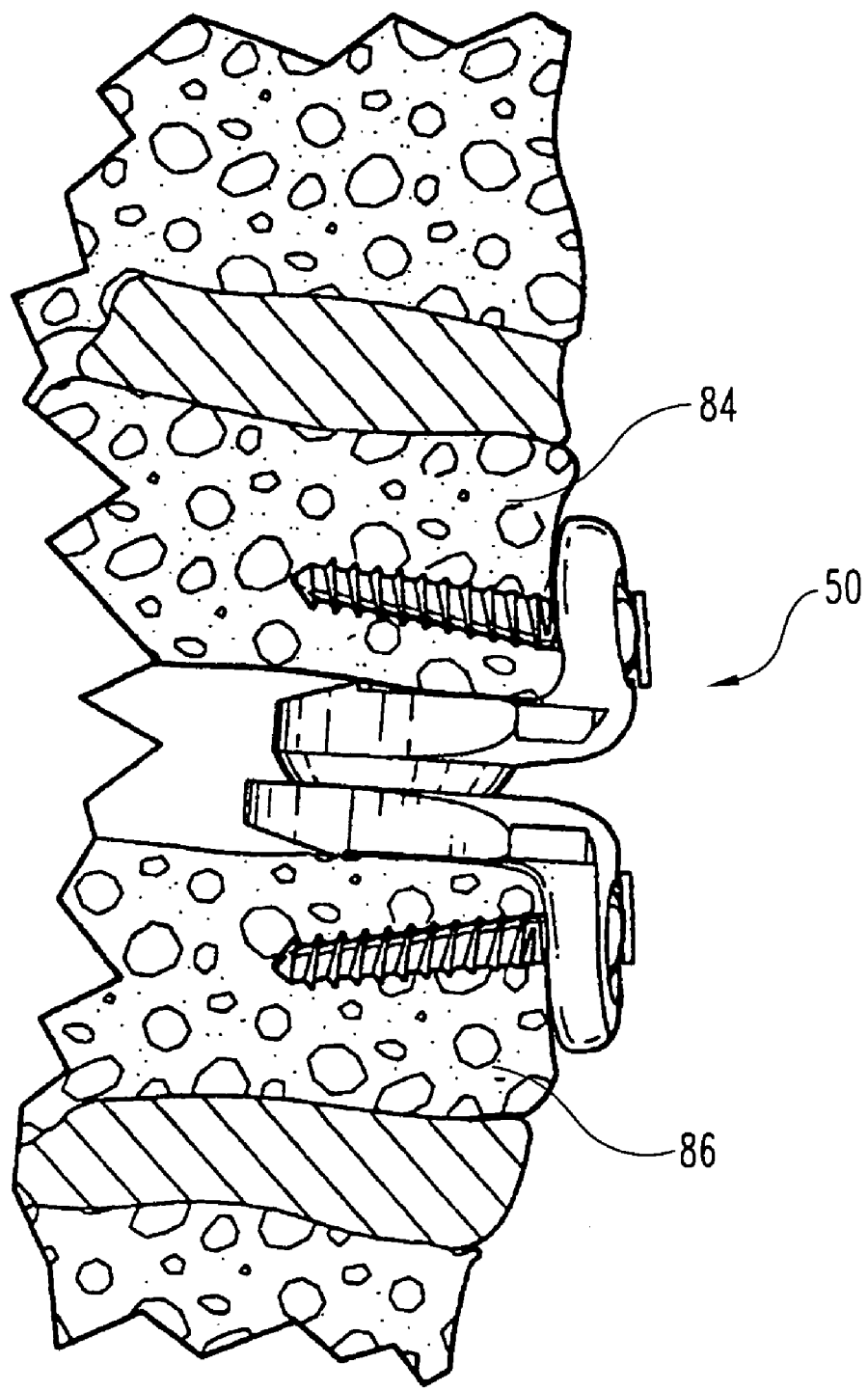
FIG. 7 is an elevated, side view in partial section of the spinal implant of FIG. 5 disposed in a disc space between a pair of vertebrae in accordance with the present invention.

FIG. 7 is an elevated side view illustrating the positioning of spinal implant 50 in a disc space between two adjacent cervical vertebrae 84 and 86. Implant 50 can be positioned in any position in the disc space.

Figure 8:
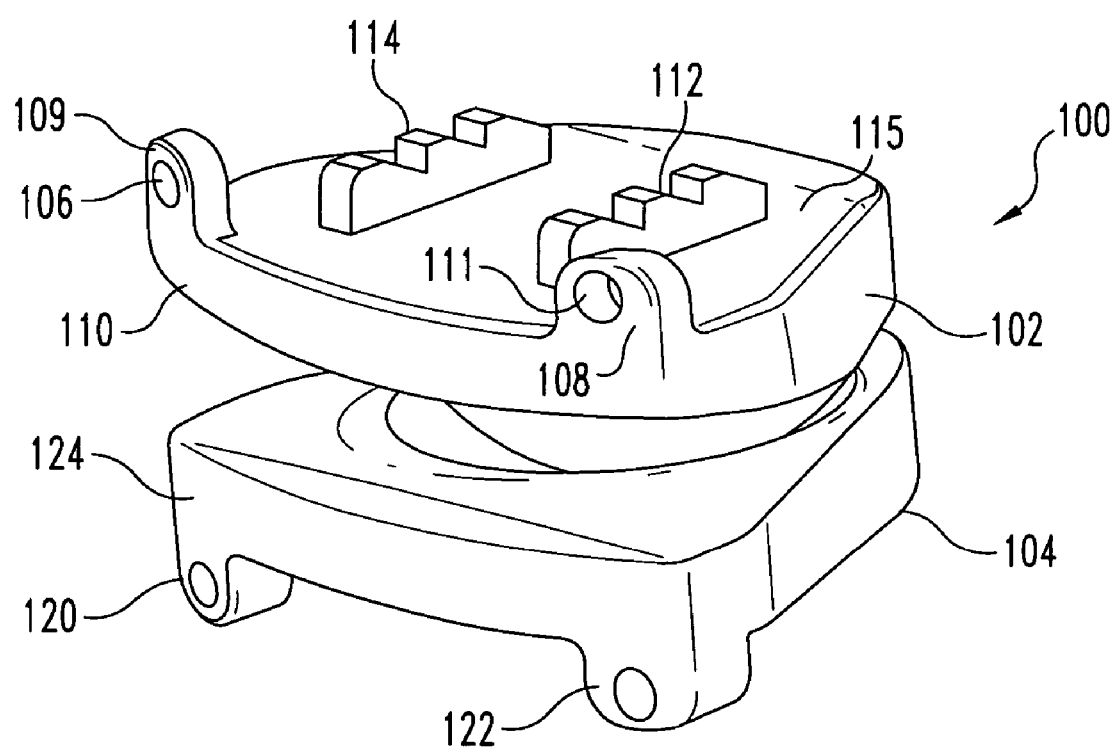
FIG. 8 is a perspective view of another embodiment a spinal implant in accordance with the present invention.

FIG. 8 is a perspective view of yet another embodiment of a spinal implant 100 in accordance with the present invention. Implant 100 is provided as an assembly that includes two basic, separable components: a first or upper portion 102 and a second or lower portion 104. Upper portion 102 can be provided substantially as has been described for upper portion 52 of implant 50. Additionally, upper portion 102 includes two flanges 106 and 108 that are configured to overlay bone tissue. Preferably flanges 106 and 108 are configured to overlay the anterior vertebral body wall portion. Each flange 106 and 108 has at least one bore or aperture 109 and 111, respectively, through which a bone fastener can be inserted. Additionally, a first, upper surface 110 includes two rails 112 and 114 extending therefrom. Rails 112 and 114 are linear and extend along the upper, bone engaging surface 115 parallel to each other. However, it will be understood that rails 112 and 114 need not be linear or parallel to each other. The two rails 112 and 114 each can include teeth or ridges and other surface structures, as noted below, to provide a secure engagement with the opposing endplate of an adjacent vertebra (not shown).

Lower portion 104 can be provided substantially as has been described for lower portion 54 of implant 50. Further, lower portion 104 includes two flanges 120 and 122 extending downwardly from an anterior wall 124 (each flange 120 and 122 can include at least one bore or aperture) and a pair of rails as has been described for the upper portion 102.

Figure 9:
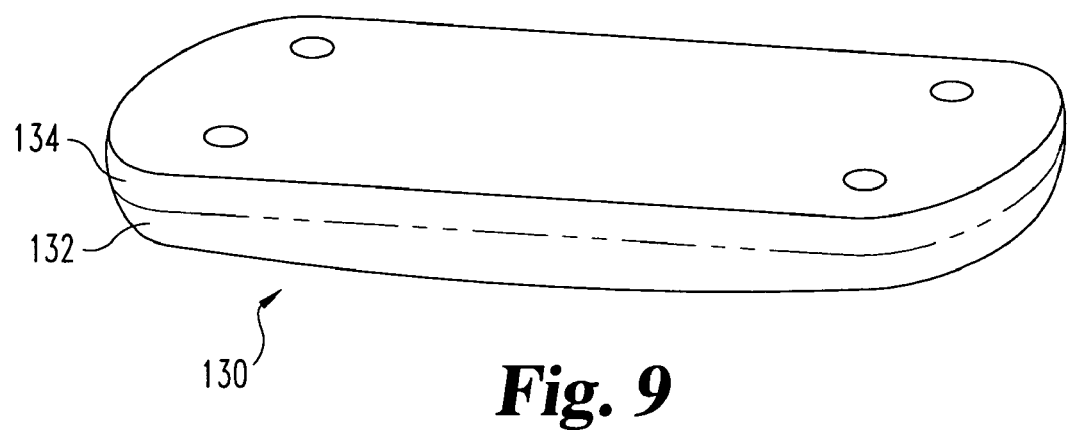
FIG. 9 is a perspective view of one embodiment of a bone plate in accordance with the present invention.

FIG. 9 is a perspective view of one embodiment of a bone plate 130 in accordance with the present invention. Bone plate 130 can comprise a metal matrix composite described more fully below. Bone plate 130 is illustrated as a laminated structure with two layers. It is to be understood that laminated bone plates comprising three, four, five, or more layers are considered to be included within the scope of the present invention. The different layers can be formed of the same or different constituents. If the layers are formed of the same constituents, then the two layers may be fabricated differently to exhibit differing properties.

In the illustrated embodiment, bone plate 130 includes a first layer 132. Layer 132 is provided to contact or engage with bone tissue. In one embodiment, layer 132 comprises a material that can include a porous metal or a porous metal matrix composite discussed more fully below. The porous metal matrix composite material can be impregnated with a first therapeutic composition or agent. For example, the therapeutic composition can include one or more of the therapeutic agents, such as a drug, a bone growth inducing component or factor, nutrients, hormones, analgesics, antibiotics, antimicrobials, antifungal, and combinations of these components. The therapeutic composition or agent can slowly diffuse out of or adhere into the porous matrix to provide a beneficial effect. For example, faster osteointegration to the bone defect or disorder or elution of the therapeutic agent to the surrounding tissue and/or the patient.

Additionally, the porous matrix can exhibit an additional beneficial effect by providing a porous substrate for tissue integration or ingrowth into the plate to facilitate secure engagement of the plate with the bone or surrounding tissue.

In yet another embodiment, bone contacting surfaces such as surface or layer 132 can include a sintered layer over an integrated porous layer to attain bimodal porosity. The differing layers can be used to absorb one, two or more therapeutic agents and allow two or more elution rates for the agents.

Bone plate 130 also includes a second layer 134. In use, second layer 134 can be positioned opposite the bone defect, disorder, or bone tissue. Second layer 134 can be composed of a) comprises a metallic material, b) a metal matrix composite, which can be the same or different from layer 132, or c) a biocompatible polymeric material, which can be either a biodegradable or a biostable material. Additionally, layer 134 can be impregnated with a second therapeutic composition or agent that is the same or different from the first therapeutic composition. The porous matrix of the first layer and/or the second layer can also serve to increase the structural integrity of the laminated structure by allowing the two layers to adhere to each other using a mechanical interlocking mechanism where material from one (or both) of the layers can be integrated within the porous structure when present in the opposing layer.

On the bone contacting surfaces, porous or not, one or more additional layers can be incorporated. The additional layer(s) can be include sintered beads, a ceramic material, such as, hydroxyapatite etc to promote bone ingrowths, or one or more reservoirs, for example, one large reservoir or bimodal reservoirs (inner and outer) for elution and delivery of one or more therapeutic agents.

Figure 10:
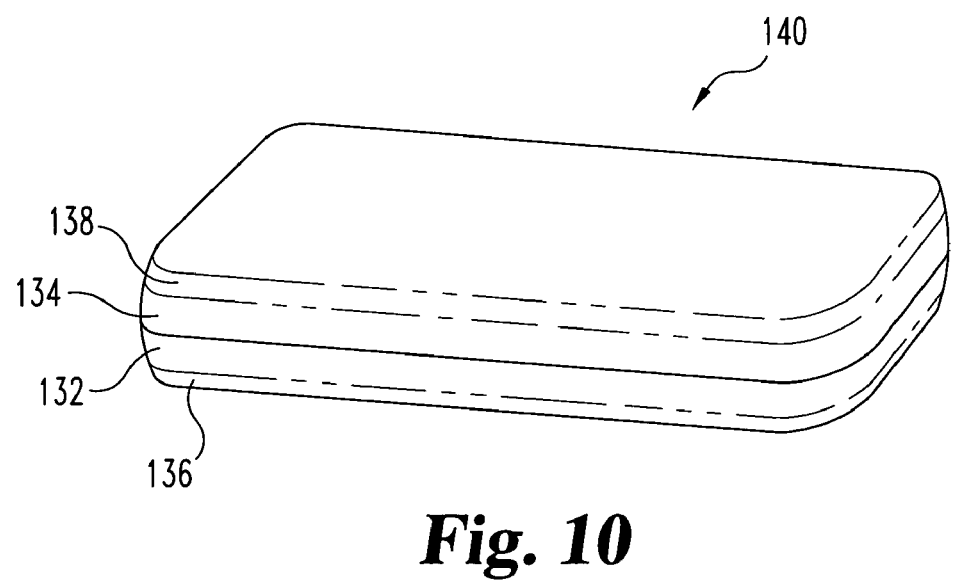
FIG. 10 is a perspective view the of bone plate of FIG. 9 with a polymeric coating in accordance with the present invention.

FIG. 10 is a perspective view of yet another embodiment of a bone plate 140 in accordance with the present invention. Bone plate 140 is a tetra-laminated structure and can include the basic components or layers as described above for plate 130. Consequently, the same reference numbers will be used to refer to similar or identical components. Bone plate 140 includes a first layer 132 and a second layer 134 as described above. First layer 132 can be coated with a polymeric material 136. Material 136 can be disposed between first layer 132 and the bone tissue. Polymeric material 136 can comprise a biodegradable or biostable agent. Further, the polymeric material can, but is not required to, include a therapeutic composition or agent either absorbed within the polymeric material or within pores formed in the polymeric material. The therapeutic agent impregnated in the polymeric material can either replace or be used in addition to the therapeutic agent absorbed within first layer 132. Varying the constituency, structure, composition and thickness and properties of the polymeric material can vary the rate of release of the encapsulated therapeutic composition. If the first layer 132 also includes a therapeutic composition, the resulting medical implant can exhibit at least two distinct drug release rates or exudation profiles.

A second coating 138 coats second layer 134. Second coating 138 can be provided as described for first polymeric material 136. However, it will be understood that the polymeric material and/or therapeutic composition for the second coating can, but need not, be the same as that in the polymeric material for the first coating.

Examples of suitable polymers for use in the present invention include a wide variety of biocompatible polymers. Specific examples of non-degradable polymers include but are not restricted to: acrylics, fluorocarbons, hydrogels, polyacetal, polyamide, polycarbonate, polyester, poly (aryl ether ketone) (PAER), poly(ether ketones) (PEK), poly(ether ether ketones) (PEEK), polyimides, polyolefins, polystyrenes, polysulfones, polyurethanes, poly(vinyl chloride) (PVC), poly (ether, ketone, ketone) (PEKK), silicone rubbers, and polyethylene. Examples of bio-degradable polymers for use in the present invention include, but are not limited to, poly(amino acids), polyanhydrides, polycaprolactones, polylactates (PLA), polyglycolates (PGA), poly (lactic-glycolic acid) (PLG), and polyorthoesters.

Figure 11:
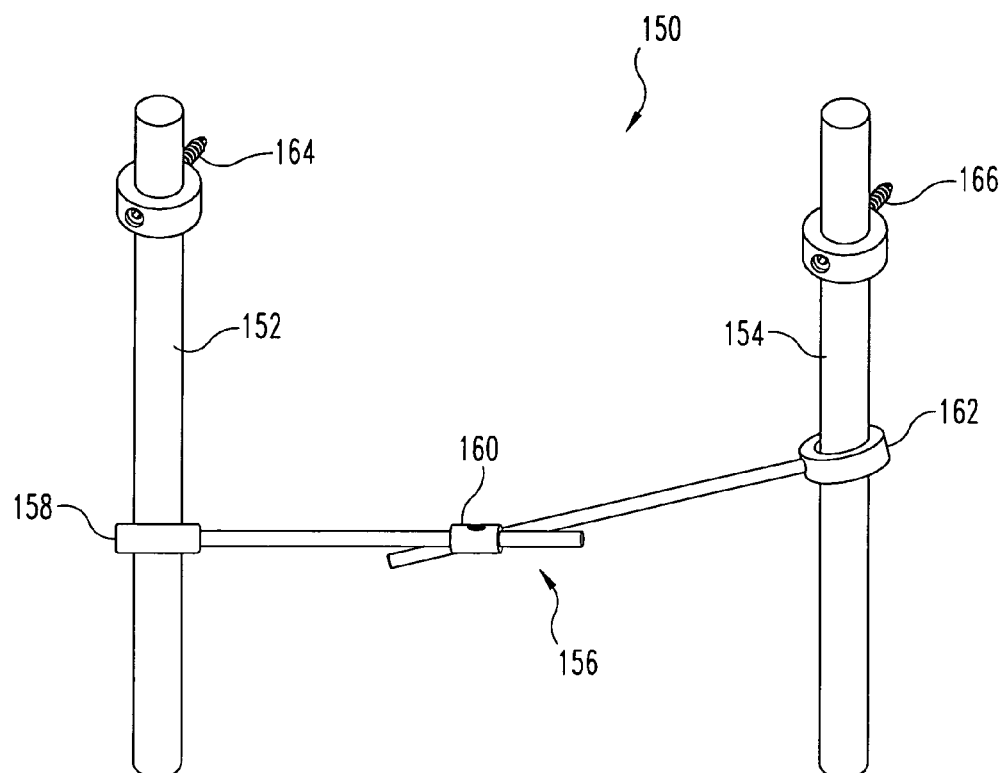
FIG. 11 is a perspective view of a spinal rod assembly in accordance with the present invention.

FIG. 11 is a perspective view of a spinal rod assembly 150 comprising a first spinal rod 152, a second spinal rod 154, and an interconnection assembly 156. In the illustrated embodiment, spinal rods 152 and 154 can be provided as a metal matrix composite comprising a reinforcing component dispersed therein. Additionally, if desired, one or more components of interconnection assembly 156 can be provided as a metal matrix composite.

In a preferred embodiment, the interconnection assembly 156 includes a first connecting rod member 158, an interconnection element 160, and a second connecting rod member 162. Examples of spinal rod assemblies can be found in the following patents: U.S. Pat. Nos. 4,641,636; 5,147,360; 6,293,949; and 6,152,927. Rods 152 and 154 and/or connecting rods 158 and 162 can be secured to portions of the spine, particularly to selected vertebral bodies using bone fasteners 164 and 166. Typically, two or more bone fasteners are used to attach each rod to the spine.

The spinal rod assembly 150 is provided to include one or more components formed of a metal matrix composite to provide distinct advantages in that the connection between one or more of the spinal rod connectors 158 and 162 with the respective spinal rods 152 and 154 provide enhanced strength and resistance to slippage of the interconnection assembly. This provides obvious advantages in minimizing the risk of further damage and requiring revisitation to either correct and/or retighten one or more components of a spinal rod assembly 150.

In a separate embodiment, only a section of the rod can be a composite material for use in applications were varying mechanical properties such as stiffness along the length of the rod is desired.

Figure 12:
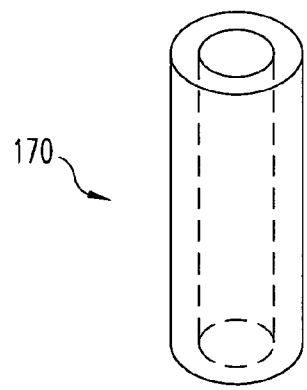
FIG. 12 is a perspective view of one embodiment of an implantable, porous tube prepared in accordance with the present invention.

FIG. 12 is a perspective illustration of a cylindrical tube 170. Tube 170 can be provided as a component of an implantable device such as a catheter, electrical lead of a pacemaker, a stent assembly, and the like. Tube 170 can be provided as a monolithic structure having a uniform composition throughout. The monolithic structure can be formed of a biocompatible metal or metallic matrix such as pure titanium or a titanium alloy, and a reinforcing component dispersed into the matrix. Alternatively, tube 170 can be provided as a laminated structure similar to bone plates 130 and 140. In either embodiment, tube 170 can be provided with a porous exterior or interior surface to allow impregnation of either an osteogenic material/agent or other therapeutic agent, which can slowly leach out into the surrounding tissue. In addition, a coating, or sintered particles or beads, can be incorporated on the exterior surfaces to accomplish a desired therapeutic treatment.

Figure 13:
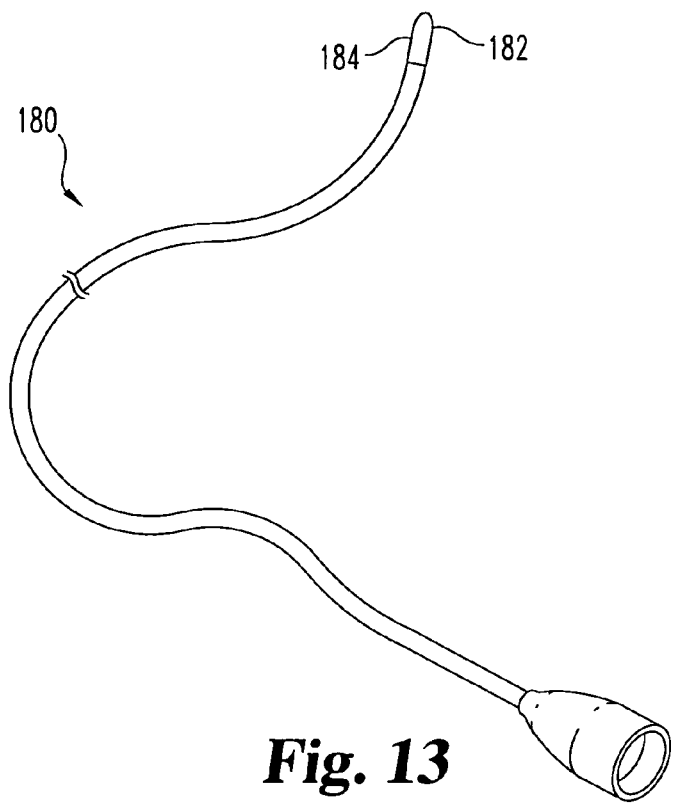
FIG. 13 is a perspective view of one embodiment of a catheter in accordance with the present invention.

FIG. 13 is a perspective view of one embodiment of a catheter 180 comprising a implantable, metallized portion 182. In the illustrated embodiment, the implantable metallized portion comprises a catheter tip 184. Catheter tip 184 comprises a metal matrix composite having a reinforcing component dispersed therethrough as discussed more fully below. The metal matrix composite can include a porous metal matrix or a dense matrix depending upon the desired properties and applications. Similar to bone plates 130 and 140, the catheter tip 184 can be impregnated with one or more therapeutic agents. Additionally, tip 184 will exhibit good imaging characteristics under standard radiographic and MRI imaging techniques. This will allow the surgeon or other health care provider to monitor the catheter and surrounding tissue with greater accuracy and detail.

Figure 14:
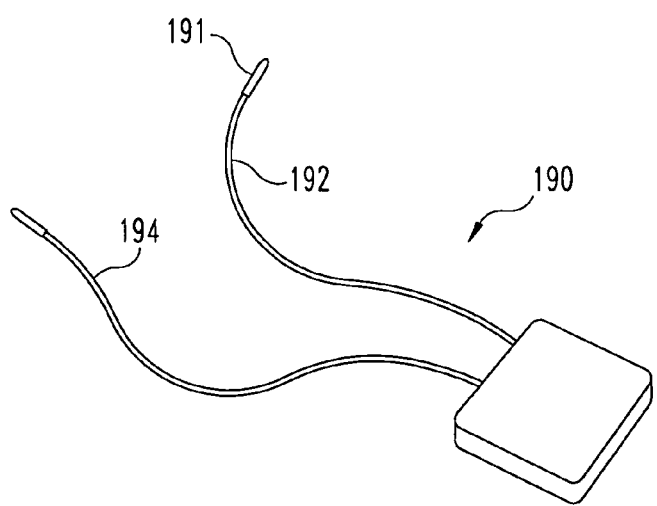
FIG. 14 is a perspective view of one embodiment of a cardiac pacemaker comprising a lead formed of a porous metal matrix composite in accordance with the present invention.

FIG. 14 is an illustration of a dual lead or dual chamber cardiac pacemaker assembly 190 with a pair of electrical leads 192 and 194. Either one or both of electrical leads 192 and 194 can comprise a metallized component or tip 191 that includes a porous metal matrix composite having a reinforcing component dispersed therethrough. The metal matrix composite in tip 191 defines a pacing electrode with a porous surface area that results in a lower polarization and interfacial impedance. Additionally, the porous metal matrix composite can provide a depot for a therapeutic composition as above discussed for the bone plate 130.

The metallic matrix composite for use in the present invention is selected to be biologically and/or pharmacologically compatible. Further, the preferred composites exhibit minimal or no toxicity, either as the bulk device or in particulate or wear debris form. The individual components in the matrix are also pharmacologically compatible. In particularly preferred embodiments, the metallic matrix composite includes at least one component that has been accepted for use by the medical community, particularly the FDA and surgeons.

The metal matrix composite of the present invention includes at least one base metal or metal alloy that provides a metal matrix and a reinforcing component interspersed within the metal matrix. As noted above, the base metal or metal alloy can be selected from a variety of biocompatible metals and metal alloys. Specific examples of biocompatible metals and metals for use in the present invention include titanium, titanium alloys, zirconium, niobium, stainless steel, cobalt and its alloys, tantalum and its alloys, and mixtures of these materials. In preferred embodiments, the metal matrix composite includes a commercially pure titanium metal (CpTi) or a titanium alloy. Examples of titanium alloys for use in the present invention include Ti-6Al-6V, Ti-6Al-6V-2Sn, Ti-6Al-2Sn-4Zr-2Mo, Ti-V-2Fe-3Al, Ti-5Al-2.5Sn, and TiNi. These alloys are commercially available in a purity sufficient for the present invention from one or more of the following venders: Allvac; Timet Industries; Specialty Metals; and Teledyne WaChang.

The metal matrix composite also includes a reinforcing component as a discrete component of the matrix. The reinforcing component can be observed as a separate phase in the metal matrix composite. In selected embodiments, the reinforcing component is a crystalline structure exhibiting a distinct grain morphology and/or size from that observed in the bulk matrix. While observed as a discrete component of the bulk matrix, it is believed that the reinforcing component imparts or influences the microstructure of the surrounding metallic matrix.

The reinforcing component imparts enhanced wear characteristics to the matrix. The selection of the reinforcing component and selection of specific fabricating procedures provides a metal matrix composite with higher hardness, improved wear resistance, improved strength, and increased tissue integration and ingrowth.

In preferred embodiments, the reinforcing component is a hard material and/or a refractory material. Examples of reinforcing components for use in the present invention include ceramics, refractory metals, metal carbides, metal nitrides, metal borides, and diamonds. Specific examples of reinforcing components for use in the present invention include W, TiC, TiN, $TiB_2$, TiAl, WC, $BC_4$, BN, diamond, zirconium oxide, aluminum oxide, and mixtures thereof.

The metal matrix composite comprises a sufficient amount of the reinforcing component to provide a composite having suitable hardness to resist or reduce either wearing away under stress and/or repeated movement. This can be particularly important for articulating implants that are configured to bear against either another hard surface or a mating component such as found in a disc or nucleus pulposus prosthesis, knee prosthesis, hip prosthesis, and other wear couples.

The reinforcing component can be added to the matrix in a desired amount. The desired amount can be selected for the intended application of the device. For example, an amount of the reinforcing component added to the matrix to provide an implant having one or more desired wear, imaging, and strength characteristic(s). It is highly desirable that the implanted device not wear at a rate sufficient to require replacement. Consequently, for a disc prosthesis, it is desirable that the metal matrix composite be hard and provide the prosthesis with excellent wear characteristics.

The implants formed of the metal matrix composite can be further treated as desired for a particular application. For example, the surfaces of the implant, whether composed of the metal matrix composite, an alloy, etc., can be subjected to secondary ion implantation, surface hardening (carbonizing, nitriding, carbonitriding), interstitial hardening can be employed on the articulating surfaces.

Additionally, medical implants may be fabricated to a high degree of precision and under strict tolerances. Depending upon the manufacturing techniques, which are discussed below more fully, fabrication of the medical device may require extensive machining and/or finishing steps. Extremely hard materials are equally hard to machine, which can be expensive and time consuming. Consequently, the proper selection of the amount of reinforcing component incorporated into the metal matrix composition is an important aspect to consider when designing and fabricating the implantable medical devices of the present invention.

In one embodiment, the metal matrix composition can include between about 1 wt % and about 90 wt % of the reinforcing component, based upon the total weight of the resulting metal matrix composition. More preferably, the metal matrix composite of the present invention includes between about 10 wt % and about 80 wt % of the reinforcing component; still more preferably, the metal matrix composite includes between about 10 wt % and about 40 wt % of the reinforcing component. In particular applications, it may be desirous to include between 10 wt % and 30 wt % of the reinforcing component into the metal matrix composition.

The metal matrix composite of the present invention can be fabricated to exhibit extreme hardness and increased wear characteristics. By incorporating a desired amount of the reinforcing component into the metal matrix, the hardness of the resulting composition can be significantly increased. The metal matrix composites according to the present invention can be fabricated over a wide hardness range depending upon the composition of the metal matrix, the reinforcing component, the shape and size of the particles, and post thermal and/or mechanical treatment. The metal matrix composites for use in the present invention can be prepared to exhibit a hardness of greater than about 20 Rc, or greater than about 45 Rc.

As noted above, the reinforcing component can exist in the metallic matrix as discrete particles or as a separate phase. The shape (circular, irregular, high aspect ratio, etc) of the reinforcing component can be selected to attain specific properties, such as isotropic or non-isotropic. In addition particle size can play an important role. The particles can be found either as platelets, grains, whiskers, or slivers depending upon the method of preparation, the identity of metallic matrix composition, the identity of the reinforcing component, and the amount of the reinforcing component added to the matrix or any secondary fabrication steps such as casting.

The metal matrix composite can be provided with a wide variety of microstructures. In preferred embodiments, the metal matrix composite is provided to have an extremely fine microstructure for the matrix material. The grain structure for the matrix material can be tailored depending upon the method of manufacture. In one specific example of a metal matrix composite, the reinforcing component can exhibit a grain size from about 2μ to about 50μ. In specific embodiments, the reinforcing component can be found in the matrix in a substantially uniform size distribution. In other embodiments in a single matrix composite, the reinforcing component can in exist in varying sizes, for example, in an averaged bimodal average grain size or an averaged multimodal grain sizes. Grain size can be controlled by starting particle size, sintering temperature, post hipping heat treatment, mechanical and thermo-mechanical processing, just to name a few processing parameters.

The metal matrix composites of the present invention can exhibit various densities depending upon the method of manufacture. High density matrixes find particular advantageous use in implants with surfaces that bear against and either rotate and/or slide against each other.

For implants that have surface that might be subject to high wear conditions, high density matrixes are preferable. Consequently, these metal matrix composites for use in the present invention can have a density of greater than about 80% or 85%. More preferably, the metal matrix composite of the present invention can have a density of greater than about 90%; more preferably, between about 95% and 100%.

Figure 15:
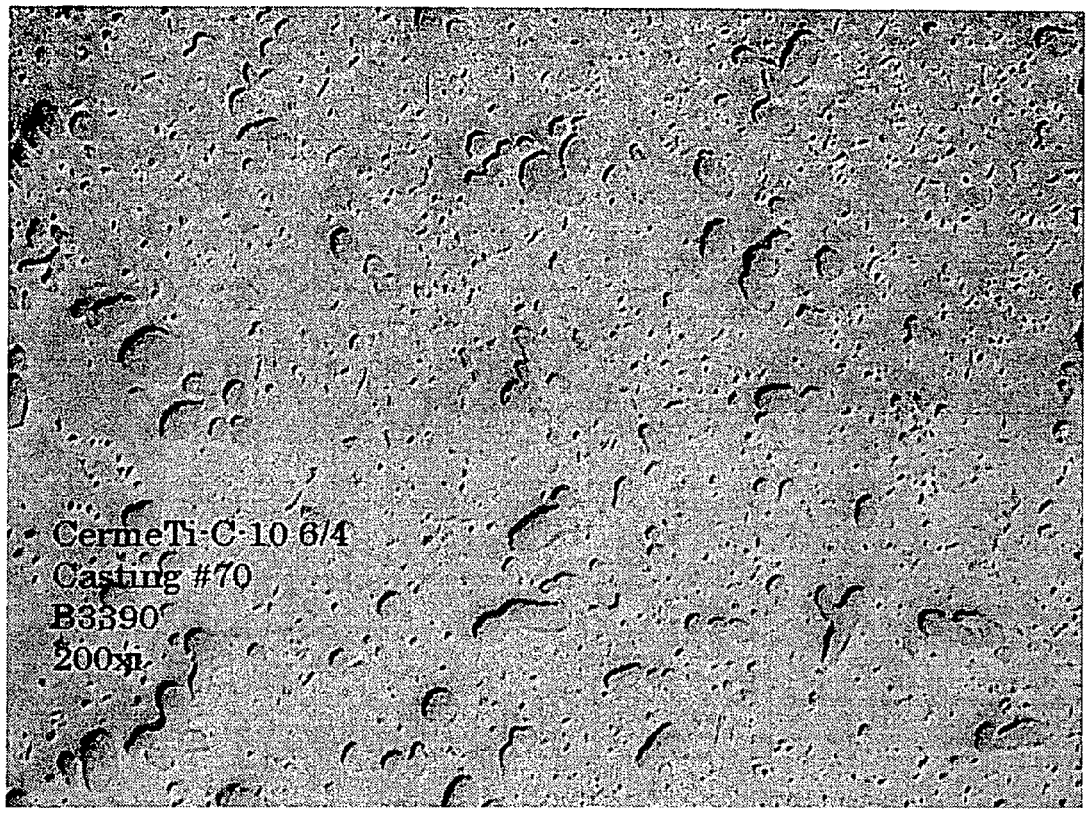
FIG. 15 is a scanned image of a micrograph of a metal matrix composite comprising 10 wt % TiC dispersed in a Ti-6Al-4V matrix.

FIG. 15 is a scanned image of a micrograph of a metal matrix composite including Ti-6Al-4V and 10-wt % TiC dispersed therein. Reference number 198 refers to the bulk Ti-6Al-4V matrix, and reference number 199 refers to the TiC particles. The material was prepared by powder compaction then cast. Following casting, a rod can be processed further to modify mechanical properties, as needed Phases of the titanium metal matrix can contain more than one phase; typically alpha and beta phases are found. The ratio of alpha to beta phases can vary. For example, in 10-wt % TiC in Ti-6Al-4V, the alpha phase predominated, while in the 10 wt % W in Ti-6Al-4V, the alpha and beta phases were found in roughly the same ratio. Additionally, the area of the matrix material immediately surrounding the reinforcing component can differ from the bulk matrix. For example, the area immediately surrounding the W in Ti-6Al-4V was almost exclusively beta phase. Consequently, the identity (and amount) of the reinforcing component in the matrix influences the microstructure of the matrix material.

In one fabrication process, the metal matrix composite can be prepared by first blending the metal matrix material and the reinforcing component to provide a uniform powdered mixture. Next, the uniform powdered mixture is subjected to pressure such as cold isostatic pressure. This provides a mechanical bond between the microcomposited materials. However, since the temperature is maintained below the melting temperature of either the reinforcing component or the metal matrix composite, no diffusion occurs between the two components.

In alternative embodiments, the porous metal matrix composite can be manufactured using hot isostatic pressing (HIP) usually under vacuum or an inert atmosphere, i.e., nitrogen argon, or mixtures thereof. The powdered mixture is heated to a temperature less than the melting temperature of either the metal matrix or the reinforcing component.

Figure 16:
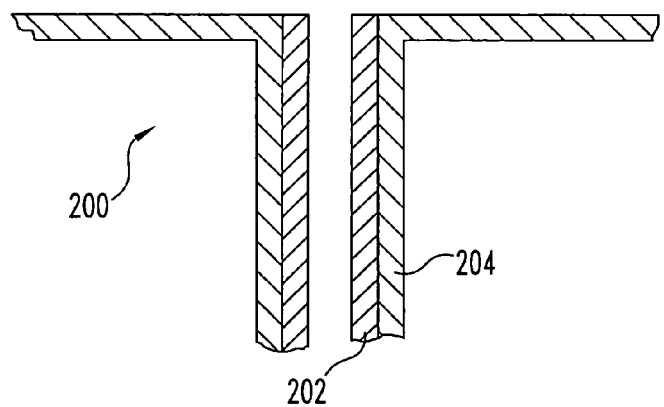
FIG. 16 is a partial view in full section of a multi-layered construct in accordance with the present invention.

FIG. 16 is a partial view in full section of a layered construct 200 in accordance with the present invention. Layered construct 200 can represent any of the implantable devices described above more fully. As can be seen in the layered construct 200 can compose two layers, 202 and 204, which can be two different materials or matrices.

Figure 17:
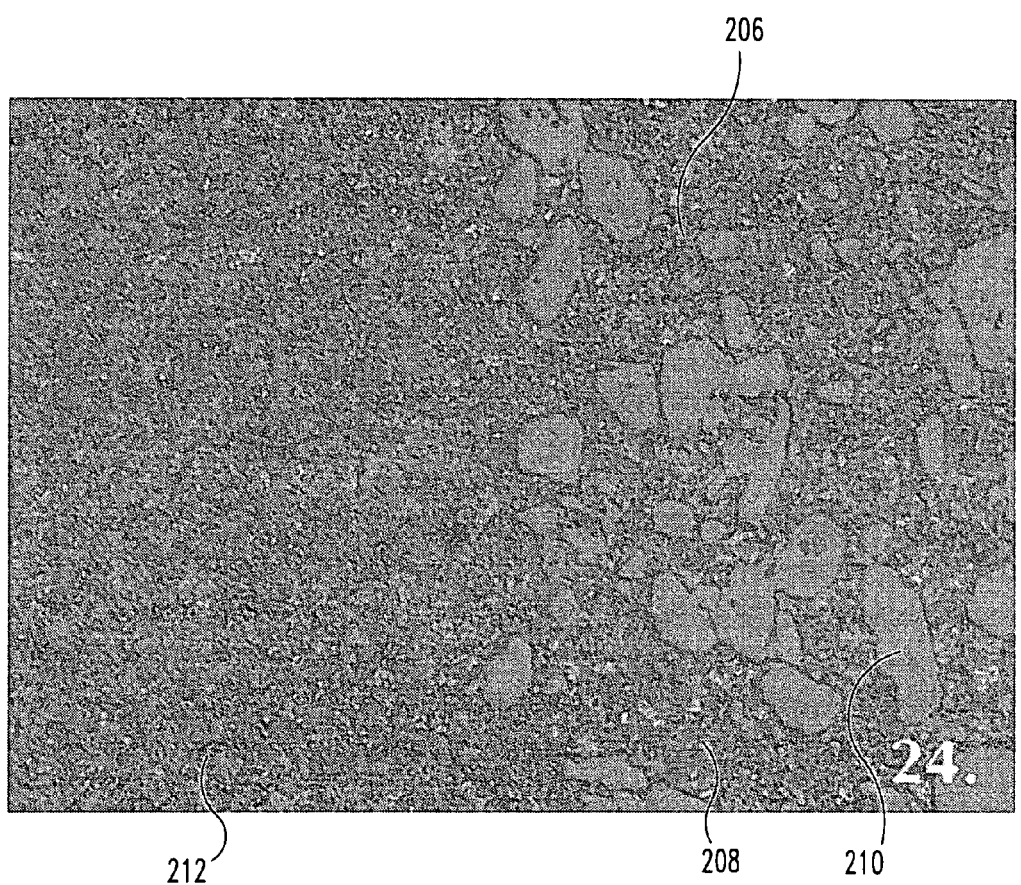
FIG. 17 is a scanned image of a micrograph of the construct of FIG. 16.

Referring additionally to FIG. 17, which is a scanned image of a micrograph of a metal matrix composite 206 that can be used in construct 120, the microstructure of the layers can be readily observed. Metal matrix composite 206 includes a first layer 208 of a metal matrix composite with a reinforcing component 210 dispersed within a metal matrix 206. The first layer 208 is laminated over a second layer 212. Second layer 212 includes little or no reinforcing component dispersed with in the matrix 210. The layer construct can be prepared by laser melting and deposition of a composite powder on a substrate or by using sintering and either cold isostatic pressing (CIP) or hot isostatic pressing (HIP) techniques.

In other embodiments, the implants according to the present invention comprising a metal matrix composite that can be fabricated using a metal injection molding (MIM) technique. The metal matrix material, the reinforcing component, and an organic binder can be blended together. The resulting mixture can then be injected molded into a near net shape of a desired implant. This technique can allow rapid fabrication of complex shapes and implant designs with minimal finish machining. The molded article or "green" article can subsequently be treated using a variety of techniques including CHIP, CIP, HIP, sintering, and densifying as is known in the art.

In other embodiments, the implants comprising a highly dense metal matrix composite of the present invention can be prepared by a variety of rapid prototyping techniques. Such techniques include stereolithography, selective laser sintering, and laser-engineered net shaping (LENS), to name just a few.

Additionally, porous metal components can be prepared by using a thermal spraying technique in which the powdered mixture is used to form a metal matrix composite using a plasma spray technique. The thermal heat may also be used as a combustion flame, an electric arc, or a plasma flame to prepare the porous metal matrix composite.

The metal matrix composite material for use in the present invention can be prepared to exhibit a predetermined, or controlled or selected porosity. When a porous metal matrix composite is desired material can be prepared to have a porosity of greater than about 5% or greater than about 10% and in another embodiment of greater than about 40%.

The pore size can be varied widely depending upon the desired application. For example, the pore size can be selected to allow bone ingrowth into the metal matrix composite. In this embodiment, the preferred pore size can be controlled or selected to be between about 10 microns (μ) and about 500μ. More preferably, the pore size can be between about 25μ and about 200μ; still more preferably between about 50μ and 150μ. The pore size as used herein can be determined according to ASTM Standard F1854-01 entitled "Standard Test Method for Stereological Evaluation of Porous Coatings on Medical Implants"

The pore size can be controlled or selected by varying the constituents of the metal matrix composite. Alternatively, the pore size can be controlled by varying selected process parameters, such as the sintering temperature and pressure. Typically, larger particles induce greater porosity into the matrix. The particle shape can also influence the porosity of the matrix. Generally, particles that do not pack well will increase the porosity of the matrix composite. For example, non-uniform or greater irregularly shaped particles, particles with a high aspect ratio, and selecting particles from a wide size distribution will increase the porosity of the matrix composite. Changing the sintering temperature also can impact the porosity of the matrix composite. Increasing the sintering temperature decreases the porosity.

The pore size can be controlled or selected to facilitate use of the implant as a depot for one or more therapeutic agents or to facilitate the release of the therapeutic agents into adjacent issue. Further, the pore size can be varied and optimized, as desired, to allow a controlled delivery rate or the agents(s); the controlled delivery rate can be for either chronic treatment and/or acute treatment.

Figure 18:
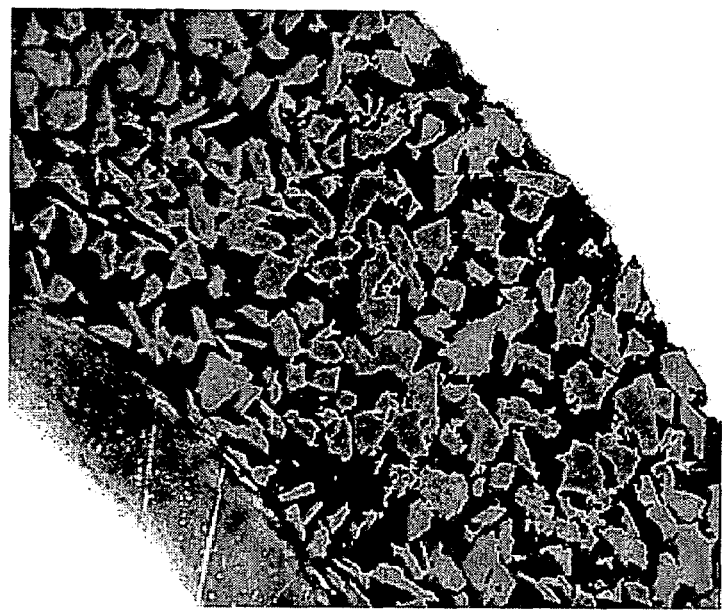
FIG. 18 is a scanned image of a micrograph of a cross section of a titanium matrix illustrating the porous structure of the material.
Figure 19:
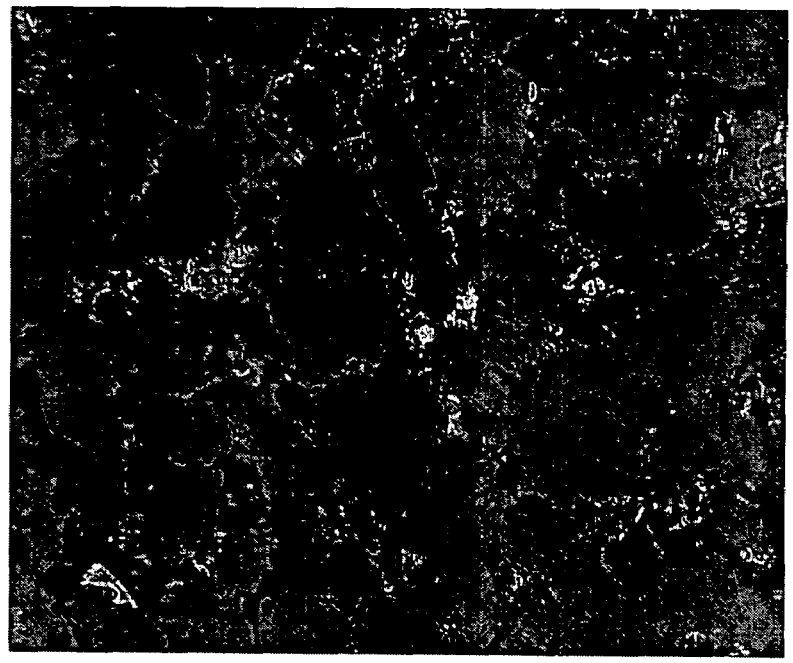
FIG. 19 is a scanned image of an enlarged view of the micrograph of FIG. 18.

FIGS. 18 and 19 are scanned images of micrographs of a cross sectional slice of a commercially pure titanium that exhibits a porous structure. The metal matrix composite of the present invention can be processed to exhibit the same or similar physical characteristics.

For the purpose of promoting further understanding and appreciation of the present invention and its advantages, the following Example is provided. It will be understood, however, that this Example is illustrative and not limiting in any fashion.

EXAMPLE

Wear Testing Comparison of a Titanium Carbide Metal Matrix Composite and Stainless Steel Three specimens in both stainless steel (316L SS) and a metal matrix composite (MMC, (TiC+Ti$_6$Al$_4$V) were prepared for multi-station, linear-reciprocating pin-on-plate wear testing. The pin specimens had spherical tips with a radius of 100 mm. Following the protocols of Varano et al. (ORS 2003), the specimens were polished and run at room temperature under a load of 9.81 N with an average speed of 26 mm/s. The lubricant consisted of 25% bovine calf serum in distilled water and was replaced frequently during the 0.75 million cycles (Mc) test. Volumetric wear was estimated from weight loss measurements. For each specimen pair, run-in wear rates (slope of a linear fit, forced through zero, for the data up to 0.1 Mc) and steady-state wear rates (slope of linear fit for data after 0.1 Mc) were calculated. The results are shown graphically in FIG. 20.

Figure 20:
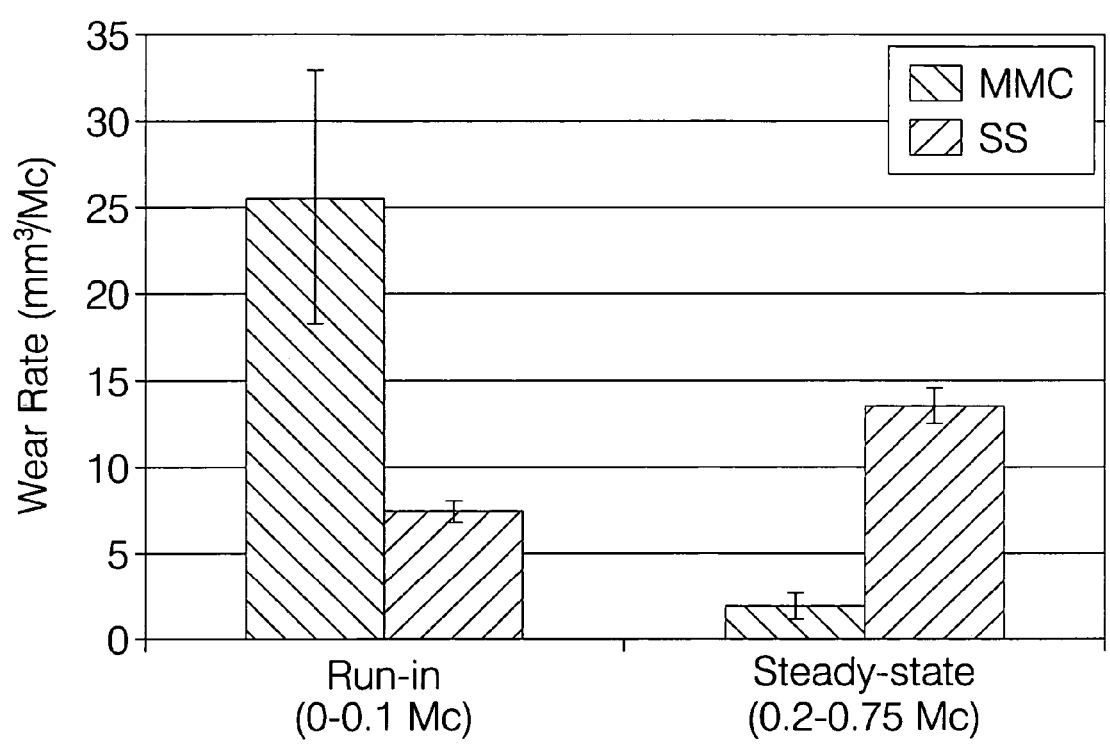
FIG. 20 is a bar graph illustrating the result of wear testing on a titanium carbide (Ti—C) metal matrix composite and a stainless steel metallic material.

In this initial study, the two material pairs had different wear rates for run-in and steady-state conditions (FIG. 20). The MMC demonstrated a higher run-in wear rate than SS but had almost an order of magnitude lower steady-state wear rate. Thus, at 0.75 Mc, the MMC had a substantially lower wear amount than the SS as well as a lower wear rate. Also, after 0.4 Mc, one station with a SS pairing leaked, giving much higher wear rates under dry conditions, and thus it was excluded subsequently from the tests.

As shown in the present study, the MMC, (TiC+Ti$_6$Al$_4$V) exhibited superior wear performance. Thus, from a tribological viewpoint, titanium-based MMC is a feasible material for metal-metal cervical spine implants, in that it has shown superior wear performance compared with the currently used SS.

The present invention contemplates modifications as would occur to those skilled in the art without departing from the spirit of the present invention. In addition, the various procedures, techniques, and operations may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Any reference to a specific direction, for example, references to up, upper, down, lower, and the like, is to be understood for illustrative purposes only or to better identify or distinguish various components from one another. Any reference to a first or second vertebra or vertebral body is intended to distinguish between two adjacent vertebrae and is not intended to specifically identify the referenced vertebrae as first and second cervical vertebrae or the first and second lumbar, thoracic, or sacral vertebrae. These references are not to be construed as limiting any manner to the medical devices and/or methods as described herein. Unless specifically identified to the contrary, all terms used herein are used to include their normal and customary terminology. Further, while various embodiments of medical devices having specific components and structures are described and illustrated herein, it is to be understood that any selected embodiment can include one or more of the specific components and/or structures described for another embodiment where possible.

Further, any theory of operation, proof, or finding stated herein is meant to further enhance understanding of the present invention and is not intended to make the scope of the present invention dependent upon such theory, proof, or finding.

What is claimed is:

1. A spinal implant assembly for insertion between adjacent first and second vertebrae, said implant comprising:
   a first plate including a first surface configured to engage the first vertebra and an opposite second surface, and
   a second plate including a third surface configured to engage the second vertebra and an opposite fourth surface having a bearing portion configured to engage the second surface of the first plate, wherein said first and second plates comprise a metal matrix composite including a metallic matrix and a reinforcing component dispersed within the metallic matrix; and
   wherein the first plate exhibits a concentrate gradient of the reinforcing component decreasing from the first surface to the second surface.

2. The spinal implant assembly of claim 1 wherein the reinforcing component is a ceramic.

3. The spinal implant assembly of claim 1 wherein the reinforcing component is an intermetallic material.

4. The spinal implant assembly of claim 1 wherein the first surface of the first plate has a porosity of greater than about 5%.

5. The spinal implant assembly of claim 4 wherein the first surface of the first plate has a porosity of greater than about 10%.

6. The spinal implant assembly of claim 4 wherein the metallic matrix material is impregnated with one or more therapeutic agents.

7. The spinal implant assembly of claim 6 wherein the metallic matrix material is impregnated with a bone growth-inducing agent.

8. The spinal implant assembly of claim 4 wherein the metallic matrix material is impregnated with a bone growth-inducing agent.

9. A spinal implant assembly for insertion between adjacent first and second vertebrae, said implant comprising:
   a first plate including a first surface configured to engage the first vertebra and an opposite second surface, and
   a second plate including a third surface configured to engage the second vertebra and an opposite fourth surface having a bearing portion configured to engage the second surface of the first plate, wherein said first and second plates comprise a metal matrix composite including a metallic matrix and a reinforcing component dispersed within the metallic matrix; and
   wherein the first plate or the second plate comprises a metal matrix composite having a bimodal porosity.

10. The spinal implant assembly of claim 9 wherein the metallic matrix comprises a titanium, titanium aluminum alloy, zirconium or niobium or a mixture thereof.

11. The spinal implant assembly of claim 10 wherein the reinforcing component is selected from the group consisting of: TiC, $TiB_2$, TiN, TiAl, WC, $BC_4$, BN, diamond, $ZrO_2$, $Al_2O_3$, and mixtures thereof.

12. The spinal implant assembly of claim 9 wherein the metallic matrix composite includes between about 1 wt % and about 90 wt % of the reinforcing component, based upon the total weight of the metallic matrix composite.

13. The spinal implant assembly of claim 12 wherein the metallic matrix composite includes between about 20 wt % and about 80-wt % of the reinforcing component, based upon the total weight of the metallic matrix composite.

14. The spinal implant assembly of claim 13 wherein the metallic matrix composite includes between about 10 wt % and about 30-wt % of the reinforcing component, based upon the total weight of the metallic matrix composite.

15. The spinal implant assembly of claim 9 wherein the second surface of the first plate comprises a convex protuberance and the fourth surface of the second plate comprises a concave receptacle to receive the convex protuberance.

16. The spinal implant assembly of claim 9 wherein the first plate and the second plate are configured to allow translational and rotational movement of the first plate relative to the second plate.

17. The spinal implant assembly of claim 9 wherein the first surface comprises bone-engaging structures.

18. The spinal implant assembly of claim 17 wherein the bone engaging structures include one or more of: ridges, teeth, grooves, rails, and wire mesh.

19. The spinal implant assembly of claim 9 comprising a flange extending at an angle oblique to the first surface and positioned to overlay bone tissue when the first surface engages the first vertebra.

20. The spinal implant assembly of claim 9 wherein the first surface of the first plate or the third surface of the second plate has a bimodal porosity.

21. The spinal implant assembly of claim 9 wherein the metal matrix composite comprises two or more layers including a sintered layer over an integrated porous layer.

22. A spinal implant assembly for insertion between adjacent first and second vertebrae, said implant comprising:
   a first plate including a first surface configured to engage the first vertebra and an opposite second surface, and
   a second plate including a third surface configured to engage the second vertebra and an opposite fourth surface having a bearing portion configured to engage the second surface of the first plate, wherein said first and second plates comprise a metal matrix composite including a metallic matrix and a reinforcing component dispersed within the metallic matrix; and
   wherein the first plate comprises a first metal matrix composite and the second plate comprises a second metal matrix composite different from the first metal matrix composite.

23. The spinal implant assembly of claim 22 wherein at least one of the first and second metal matrix composites is selected to exhibit a surface hardness of at least 20 Rc.

24. The spinal implant assembly of claim 22 wherein at least one of the first and second metal matrix composites is selected to exhibit a surface hardness of at least about 45 Rc.

25. The spinal implant assembly of claim 22 wherein the metal matrix material has a density of greater than about 80%.

26. The spinal implant assembly of claim 25 wherein the metal matrix material has a density of greater than about 90%.

27. The spinal implant assembly of claim 22 wherein the reinforcing component is homogeneously dispersed throughout the metallic matrix material.

28. The spinal implant assembly of claim 22 wherein the reinforcing component is inhomogeneously dispersed throughout the metallic matrix material.

29. The spinal implant assembly of claim 22 wherein the first metal matrix composite includes a first reinforcing material and the second metal matrix composite includes a second reinforcing material different from the first reinforcing material.

30. The spinal implant assembly of claim 29 wherein the first metal matrix composite has a first porosity and the second metal matrix composite has a second porosity different from the first porosity.

31. The spinal implant assembly of claim 22 wherein the first metal matrix composite has a first porosity and the second metal matrix composite is about 100% dense.

32. The spinal implant assembly of claim 22 wherein the second surface of the first plate has a first recess, and the fourth surface of the second plate comprises an articulating element engaged with the first recess of the first plate.

33. The spinal implant assembly of claim 32 wherein the articulating element is spherical, cylindrical, elliptical, disk shaped, or wafer shaped.

34. The spinal implant assembly of claim 32 wherein the metallic matrix composite includes between about 1 wt % and about 90 wt % of the reinforcing component, based upon the total weight of the metallic matrix composite.

35. The spinal implant assembly of claim 34 wherein the metallic matrix composite includes between about 20 wt % and about 80-wt % of the reinforcing component, based upon the total weight of the metallic matrix composite.

36. The spinal implant assembly of claim 32 wherein the second plate and the articulating element are a one-piece structure.

37. The spinal implant assembly of claim 32 wherein the second plate and the articulating element are non integral.

38. The spinal implant assembly of claim 32 wherein the metallic matrix composite includes between about 10 wt % and about 30 wt % of the reinforcing component, based upon the total weight of the metallic matrix composite.

39. The spinal implant assembly of claim 32 wherein the first surface of the first plate has a porosity of greater than about 5%.

40. The spinal implant assembly of claim 32 wherein the first surface of the first plate has a porosity of greater than about 10%.

41. The spinal implant assembly of claim 32 wherein the metallic matrix material is impregnated with one or more therapeutic agents.

42. A spinal implant assembly for insertion between adjacent first and second vertebrae, said implant comprising:

a first plate including a first surface configured to engage the first vertebra and an opposite second surface, and a second plate including a third surface configured to engage the second vertebra and an opposite fourth surface having a bearing portion configured to engage the second surface of the first plate, wherein said first and second plates comprise a metal matrix composite including a metallic matrix and a reinforcing component dispersed within the metallic matrix; and wherein the first surface of the first plate has a bimodal porous structure.

43. A medical device comprising: a disc prosthesis comprising a first layer including a first metal matrix composite comprising a metal matrix and a first reinforcing component dispersed within the matrix, and a second layer including a second metal matrix composite.

44. The device of claim 43 wherein the first metallic matrix comprises a titanium, titanium aluminum alloy, zirconium, niobium, or a mixture thereof.

45. The device of claim 43 wherein the first reinforcing component is selected from the group consisting of: TiC, $TiB_2$, TiN, TiAl, WC, $BC_4$, BN, diamond, $ZrO_2$, $Al_2O_3$, and mixtures thereof.

46. The device of claim 43 wherein the first metallic matrix composite includes between about 1 wt % and about 90 wt % of the first reinforcing component, based upon the total weight of the metallic matrix composite.

47. The device of claim 46 wherein the first metallic matrix composite includes between about 20 wt % and about 80 wt % of the first reinforcing component, based upon the total weight of the metallic matrix composite.

48. The device of claim 47 wherein the first metallic matrix composite includes between about 10 wt % and about 30-wt % of the first reinforcing component, based upon the total weight of the metallic matrix composite.

49. The device of claim 43 wherein the second metal matrix composite is different from the first metal matrix composite.

50. The device of claim 43 wherein the second metal matrix composite includes a second reinforcing component different from the first reinforcing component.

51. The device of claim 43 wherein the first layer is configured to have a first porosity and the second layer is configured to have a second porosity different from the first porosity.

52. The device of claim 43 comprising one or more therapeutic agents.

53. The device of claim 43 comprising a sintered layer overlaying the first layer.

* * * * *